United States Patent

Friebe et al.

[11] 4,086,347
[45] Apr. 25, 1978

[54] 9[3-(4-PHENOXYMETHYLPIPERIDINO)-PROPYL]-ADENINES

[75] Inventors: Walter-Gunar Friebe, Darmstadt; Max Thiel, Mannheim, both of Germany; Kurt Stach, deceased, late of Mannheim-Waldhof, Germany; by Werner Plattner, administrator, Linz, Austria; Otto-Henning Wilhelms, Heddesheim, Germany; Erika von Müllendroff, Karlsruhe, Germany; Gisbert Sponer, Hemsbach, Germany

[73] Assignee: Boehringer Mannheim GmbH, Mannheim-Waldhof, Germany

[21] Appl. No.: 737,507

[22] Filed: Nov. 2, 1976

[30] Foreign Application Priority Data

Nov. 7, 1975 Germany .............................. 2550000

[51] Int. Cl.² .................... A61K 31/52; C07D 473/34
[52] U.S. Cl. .................................. 424/253; 260/252; 260/254
[58] Field of Search ................. 260/252, 254; 424/253

[56] References Cited

U.S. PATENT DOCUMENTS 3,917,596 11/1975 Winter et al. .......................... 260/252
3,996,361 12/1976 Friebe et al. .......................... 260/252

Primary Examiner—Paul M. Coughlan, Jr.
Attorney, Agent, or Firm—Burgess, Dinklage & Sprung

[57] ABSTRACT

9-[3-(4-Phenoxymethylpiperidino)-propyl]-adenines of the formula

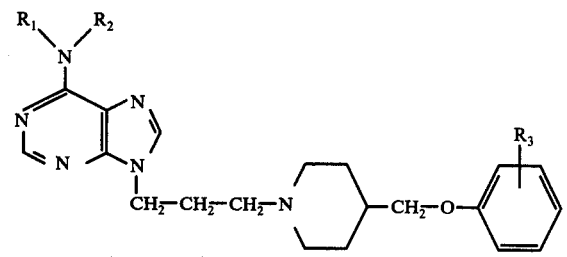

wherein
$R_1$ is a hydrogen atom or a lower alkyl radical,
$R_2$ is a hydrogen atom, a ower alkyl radical optionally substituted by hydroxyl, or a cycloalkyl radical, or
$R_1$ and $R_2$ together with the nitrogen atom to which they are attached form a heterocyclic ring, and
$R_3$ is a hydrogen atom, a halogen atom, a lower alkyl radical or a lower alkoxy radical, in the form of the free base or a salt thereof, exhibit anti-allergic, anti-inflammatory, anti-oedematous and anti-hypertensive activity.

13 Claims, No Drawings

9-[3-(4-PHENOXYMETHYLPIPERIDINO)-PROPYL]-ADENINES

The present invention is concerned with new piperidinoalkyl derivatives of purines and with the preparation thereof.

The new piperidinoalkyl derivatives of purines according to the present invention are compounds of the general formula

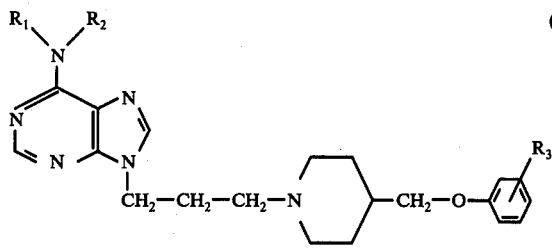

wherein $R_1$ is a hydrogen atom or a lower alkyl radical, $R_2$ is a hydrogen atom or a lower alkyl radical optionally substituted by hydroxyl or is a cycloalkyl radical or $R_1$ and $R_2$, together with the nitrogen atom to which they are attached, form a heterocyclic ring, and $R_3$ is a hydrogen or halogen atom or a lower alkyl or alkoxy radical. The compounds may be present as the free bases or as salts thereof with pharmacologically compatible acids.

The lower alkyl radicals $R_1$, $R_2$ and $R_3$ can be straight-chained or branched and contain up to 6 and preferably up to 4 carbon atoms. The cycloalkyl radicals contain 3 to 6 carbon atoms and the lower alkoxy radicals contain up to 4 carbon atoms.

The halogen atoms, when present, are preferably fluorine, chlorine or bromine atoms.

The heterocyclic ring which can be formed by $R_1$ and $R_2$, together with the nitrogen atom to which they are attached, can be, for example, a tetramethyleneimino, pentamethyleneimino or hexamethyleneimino ring.

Apart from the compounds specifically mentioned in the examples hereinbelow. The present invention also includes all compounds which contain all possible combinations of the substituents.

We have found that the new compounds according to the present invention suppress the liberation and action of histamine and can thus have an anti-allergic, anti-inflammatory and anti-oedematous action. We have also found that the new compounds according to the present invention possess an anti-hypertensive action.

The new compounds according to the present invention can be prepared by reacting a compound of the general formula

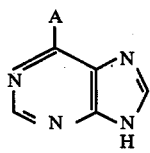

wherein A is a reactive residue or an

group, in which $R_1$ and $R_2$ have the same meanings as above, with a compound of the general formula $$X-CH_2-CH_2-CH_2-Y \qquad (III),$$

wherein X and Y are reactive residues, and with a compound of the general formula

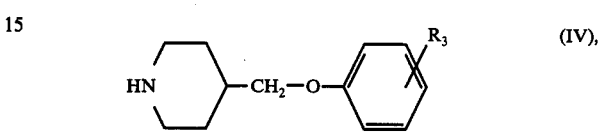

wherein $R_3$ has the same meaning as above, and, when A is a reactive group, the

group is subsequently introduced, and subsequently, if desired, the reaction product obtained is converted into a pharmacologically compatible salt.

As reactive residues X and Y in the compounds of general formula (III), there can be used, for example, chlorine or bromine atoms or mesyloxy or tosyloxy radicals. The reactive residue A in compounds of general formula (II) can be a halogen atom, preferably a chlorine or a bromine atom, as well as an alkylthio or benzylthio radical.

The process according to the present invention is preferably carried out by first condensing a compound of general formula (III) with a compound of general formula (IV) and then isolating the reaction product obtained. This intermediate is then reacted with a compound of general formula (II). The reaction is preferably carried out in an alkaline medium and preferably in a lower alcohol, for example in isopropanol, in the presence of sodium isopropylate. Under these reaction conditions, the compounds of general formula (I) are obtained, together with small amounts of isomeric derivatives substituted in the 7-position, which can, however, be removed by recrystallization of the reaction products.

Another variant of the process is first to react compounds of general formula (II) with compounds of general formula (III); subsequently, the reaction mixture obtained is reacted with compounds of general formula (IV) to give the desired end product of general formula (I).

When A is a reactive group, then the $-NR_1R_2$ group must subsequently be introduced. This can be accomplished by processes which are generally known in the field of purine chemistry.

Compounds of general formulae (II) and (III) are known from the literature and can easily be prepared from known compounds by well-known methods.

The compounds of general formula (IV) are described in our simultaneously filed co-pending Patent Application Ser. No. 737,518, filed Nov. 1, 1976, now pending.

The pharmacologically compatible salts of the compounds of general formula (I) can be prepared in the usual manner, for example, by neutralization of the compounds of general formula (I) with non-toxic inorganic or organic acids, for example hydrochloric acid, sulfuric acid, phosphoric acid, hydrobromic acid, acetic acid, lactic acid, citric acid, malic acid, salicyclic acid, malonic acid, maleic acid or succinic acid.

The new compounds according to the present invention of general formula (I) can be administered enterally or parenterally in liquid or solid form as the free base or salt. For this purpose, there can be used all the conventional forms of administration, for example, tablets, capsules, dragees, syrups, solutions, suspensions and the like. As injection medium, it is preferred to use water which contains the additives usual in the case of injection solutions, such as stabilizing agents, solubilizing agents and buffers. Additives of this type include, for example, tartrate and citrate buffers, ethanol, complex forming agents (such as ethylenediamine-tetraacetic acid and the non-toxic salts thereof) and high molecular weight polymers (such as liquid polyethylene oxide) for viscosity regulation. Liquid carrier materials for injection solutions must be sterile and are preferably filled into ampules. Solid carrier materials include, for example, starch, lactose, mannitol, methyl cellulose, talc, highly dispersed silicic acids, high molecular weight fatty acids (such as stearic acid), gelatin, agar-agar, calcium phosphate, magnesium stearate, animal and vegetable fats and solid high molecular weight polymers (such as polyethylene glycols); compositions suitable for oral administration can, if desired, contain flavoring and sweetening materials.

The following examples are given for the purpose of illustrating the present invention:

EXAMPLE 1

9-[3-(4-Phenoxymethylpiperidino)-propyl]-adenine i. The 3-(4-phenoxymethylpiperidino)-propyl chloride used as starting material is prepared as follows:

A mixture of 28.6 g (0.15 mole) of 4-phenoxymethyl-piperidine, 23.5 g (0.15 mole) of 1-bromo-3-chloropropane, 40.4 g (0.4 mole) of triethylamine and 150 ml of tetrahydrofuran is heated under reflux for 5 hours. After cooling, the reaction mixture is filtered, the filtrate is evaporated in a vacuum, the residue is extracted with diethyl ether and the extract is evaporated. There are obtained 33.6 g (84% of theory) of crude 3-(4-phenoxymethylpiperidino)-propyl chloride in the form of an oil which can be further used in this form. The pure compound is obtained by distillation and boils at 180° – 183° C/0.4 mm Hg.

The phenoxymethylpiperidinopropyl chlorides used in the subsequent examples, which are also viscous oils, can be prepared in an analogous manner.

ii. 9.45 g (0.07 mole) of adenine are added to a solution of 1.6 g (0.07 mole) of sodium in 250 ml of isopropanol and the reaction mixture heated under reflux for 10 minutes. It is then cooled and 21.4 g (0.08 mole) of 3-(4-phenoxymethylpiperidino)-propyl chloride in 50 ml of isopropanol added thereto. After stirring the reaction mixture under reflux for 6 hours, it is evaporated in a vacuum, the residue is taken up in methylene chloride, the methylene chloride solution is washed with 2N aqueous sodium hydroxide solution and subsequently with water, dried over anhydrous sodium sulfate, evaporated and the residue recrystallized from isopropanol. There are obtained 16.4 g (64% of theory) of 9-[3-(4-phenoxymethylpiperidino)-propyl]-adenine; m.p. 142° – 144° C.

The compounds set out in the following table are prepared in analogous manner:

Table I

| Example | Product and starting materials | Yield % | melting point, ° C (solvent used for recrystallization) |
|---|---|---|---|
| a) | 9-{3-[4-(2-bromophenoxymethyl)-piperidino]-propyl}-adenine from adenine and 3-[4-(2-bromophenoxymethyl)-piperidino]-propyl chloride | 44 | 154 – 155 (isopropanol) |
| b) | 9-{3-[4-(2-chlorophenoxymethyl)-piperidino]-propy}-adenine from adenine and 3-[4-(2-chlorophenoxymethyl)-piperidino]-propyl chloride | 55 | 146 – 147 (isopropanol) |
| c) | 9-{3-[4-(3-chlorophenoxymethyl)-piperidino]-propyl}-adenine from adenine and 3-[4-(3-chlorophenoxymethyl)-piperidino]-propyl chloride | 41 | 161 – 162 (isopropanol) |
| d) | 9-{3-[4-(4-chlorophenoxymethyl)-piperidino]-propyl}-adenine from adenine and 3-[4-(4-chlorophenoxymethyl)-piperidino]-propyl chloride | 38 | 171 – 172 (isopropanol) |
| e) | 9-{3-[4-(4-fluorophenoxymethyl)-piperidino]-propyl}-adenine from adenine and 3-[4-(4-fluorophenoxymetyl)-piperidino]-propyl chloride | 56 | 150 – 151 (isopropanol) |
| f) | 9-{3-[4-(2-methoxy-phenoxymethyl)-piperidino]-propyl}-adenine from adenine and 3-[4-(2-methoxy-phenoxymethyl)-piperidino]-propyl chloride | 52 | 144 – 145 (isopropanol) |
| g) | 9-{3-[4-(3-methoxy-phenoxymethyl)-piperidino]-propyl}-adenine from adenine and 3-[4-(3-methoxy-phenoxymethyl)-piperidino]-propyl chloride | 30 | 153 –155 (isopropanol) |
| h) | 9-{3-[4-(4-methoxy-phenoxymethyl)-piperidino]-propyl}-adenine from adenine and 3-[4-(4-methoxy-phenoxymethyl)-piperidino]-propyl chloride | 66 (isopropanol) | 159 – 161 |
| i) | 9-{3-[4-(2-methyl-phenoxymethyl)-piperidino]-propyl}-adenine from adenine and 3-[4-(2-methyl-phenoxy- | 38 | 143 – 145 (isopropanol) |

Table I-continued

| Example | Product and starting materials | Yield % | melting point, °C (solvent used for recrystallization) |
|---|---|---|---|
| j) | $N^6$-methyl-9-[3-(4-phenoxymethyl-piperidino)-propyl]-adenine from $N^6$-methyladenine and 3-(4-phenoxymethyl-piperidino-propyl chloride | 50 | 148 –149 (isopropanol) |
| k) | $N^6$-methyl-9-{3-[4-(4-fluorophenoxy-methyl)-piperidino]-propyl}-adenine from $N^6$-methyladenine and 3-[4-(4-fluorophenoxymethyl)-piperidino]-propyl chloride | 61 | 142 – 143 (isopropanol) |
| l) | $N^6$-ethyl-9-[3-(4-phenoxymethyl-piperidino)-propyl]-adenine from $N^6$-ethyladenine and 3-(4-phenoxymethyl-piperidino)-propyl chloride | 27 | 92 – 93 (ethyl acetate) |
| m) | $N^6$-ethyl-9-{3-[4-(4-fluorophenoxy-methyl)-piperidino]-propyl}-adenine from $N^6$-ethyladenine and 3-[4-(4-fluorophenoxymethyl)-piperidino]-propyl chloride | 35 | 100 – 102 (ethyl acetate/ ligroin) |
| n) | $N^6$-(2-hydroxyethyl)-9-[3-(4-phenoxy-methyl-piperidino)-propyl]-adenine from $N^6$-(2-hydroxyethyl)-adenine and 3-(4-phenoxymethyl-piperidino)-propyl chloride | 30 | 82 – 84 (diethyl ether) |
| o) | $N^6$-n-propyl-9-[3-(4-phenoxymethyl-piperidino)-propyl]-adenine from $N^6$-n-propyladenine and 3-(4-phenoxymethyl-piperidino)-propyl chloride | 34 | 62 – 63 (cyclohexane) |
| p) | $N^6$-n-propyl-9-{3-[4-(4-fluorophenoxy-methyl)-piperidino]-propyl}-adenine from $N^6$-n-propyladenine and 3-[4-(4-fluoro-phenoxymethyl)-piperidino]-propyl chloride | 30 | 70 – 71 (diethyl ether) |
| q) | 6-dimethylamino-9-[3-(4-phenoxymethyl-piperidino)-propyl]-purine from 6-dimethylamino-purine and 3-(4-phenoxy-methyl-piperidino)-propyl chloride | 43 | 76 – 77 (ethyl acetate/ ligroin) |
| r) | 6-pyrrolidino-9-[3-(4-phenoxymethyl-piperidino)-propyl]-purine from 6-pyrrolidino-purine and 3-(4-phenoxymethyl-piperidino)-propyl chloride | 33 | 91 – 92 (ethyl acetate/ ligroin) |
| s) | 9-{3-[4-(2-fluorophenoxymethyl)-piperidino]-propyl}-adenine from adenine and 3-[4-(2-fluorophenoxymethyl)-piperidine]-propyl chloride | 45 | 140 – 141 (ethyl acetate) |
| t) | $N^6$-methyl-9-{-3-[4-(2-fluorophenoxy-methyl)-piperidino]-propyl}-adenine from $N^6$-methyladenine and 3-[4-(2-fluorophenoxymethyl)-piperidino]-propyl chloride | 42 | 158 – 160 (isopropanol) |

EXAMPLE 2

$N^6$-n-Butyl-9-{3-[4-(4-fluorophenoxymethyl)-piperidino]propyl}-adenine 9.55 g (0.05 mole) of $N^6$-n-butyladenine are added to a solution of 1.15 g (0.05 mole) of sodium in 200 ml of isopropanol and the reaction mixture is heated under reflux for 10 minutes. After cooling, 22.8 g (0.08 mole) of 3-[4-(4-fluorophenoxymethyl)-piperidino]-propyl chloride in 50 ml of isopropanol are added thereto. After boiling under reflux for 6 hours, the reaction mixture is evaporated in a vacuum and the residue is taken up in methylene chloride, washed with 2N aqueous sodium hydroxide solution and subsequently with water, dried over anhydrous sodium sulfate, evaporated and the residue is taken up in acetone and mixed with excess saturated ethereal hydrogen chloride solution. The salt which precipitates out is filtered off and recrystallized from isopropanol. There are obtained 14.6 g (57% of theory) of $N^6$-n-butyl-9-{3-[4-(4-fluorophenoxymethyl)-piperidino]-propyl}-adenine dihydrochloride; m.p. 180° – 182° C.

The following compounds are prepared in an analogous manner:

Table II

| Example | Product and starting materials | Yield % | melting point °C (solvent used for recrystallization) |
|---|---|---|---|
| a) | $N^6$-isopropyl-9-[3-(4-phenoxymethyl-piperidino)-propyl]-adenine from $N^6$-isopropyladenine and 3-(4-phenoxy-methyl-piperidino)-propyl chloride | 33 | dihydrochloride 196 – 198 (isopropanol/ diethyl ether) |
| b) | $N^6$-n-butyl-9-[3-(4-phenoxymethyl-piperidino)-propyl]-adenine from $N^6$-n-butyladenine and 3-(4-phenoxymethyl-piperidino)-propyl chloride | 32 | dihydrochloride 201 – 202 (ethanol/ diethyl ether) |
| c) | $N^6$-cyclohexyl-9-[3-(4-phenoxymethyl-piperidino)-propyl]-adenine from $N^6$-cyclohexyladenine and 3-(4-phenoxy- | 36 | dihydrochloride 190 – 192 (ethanol/ |

| Example | Product and starting materials | Yield % | melting point ° C (solvent used for recrystallization) |
|---|---|---|---|
| | methyl-piperidino)-propyl chloride | | diethyl ether) |

EXAMPLE 3

N$^6$-n-Propyl-9-[3-(4-phenoxymethylpiperidino)-propyl]-adenine i. 6-Chloro-9-[3-(4-phenoxymethylpiperidino)-propyl]-purine used as starting material is obtained in the following manner:

A mixture of 15.4 g (0.1 mole) of 6-chloropurine, 75 ml of N,N-dimethyl formamide, 13.8 g (0.1 mole) of potassium carbonate and 26.8 g (0.1 mole) of 3-(4-phenoxymethylpiperidino)-propyl chloride is heated to 40° C for 6 hours, while stirring. The reaction mixture is then mixed with water extracted with ethyl acetate and the extract is dried and evaporated. The residue obtained is recrystallized from ethyl acetate/ligroin. There are obtained 16.2 g (42% of theory) of 6-chloro-9-[3-(4-phenoxymethylpiperidino)-propyl]-purine; m.p. 95° – 96° C.

ii. 50 ml of n-propylamine are added to a solution of 11.6 g (0.03 mole) of 6-chloro-9-[3-(4-phenoxymethylpiperidino)-propyl]-purine in 100 ml of n-propanol and the reaction mixture is heated under reflux for 6 hours. It is then evaporated in a vacuum and the residue extracted with diethyl ether. After evaporation of the solvent and recrystallization of the residue from cyclohexane, there are obtained 9.1 g of N$^6$-n-propyl-9-[3-(4-phenoxymethylpiperidino)-propyl]-adenine (74% of theory); m.p. 62° – 63° C.

The foregoing compounds can be used as such or they can be converted to salts with pharmacologically acceptable acids. They can be administered orally, as pills, tablets, capsules, powders and the like. The preferred form of oral administration is as a tablet containing 10 to 300 mg of active compound.

The compounds can also be administered parenterally. Injection solutions containing 50 mg/ml of injection solution are preferred.

With respect to the proper dosage and methods of application for the instant compounds, these are comparable to those for the commercially known compound "Fragivix", i.e, 2-ethyl-3-(4'-hydroxybenzoyl)-benzofuran. The instant compounds make possible comprehensive therapy of acute as well as chronic phlebological and capillary afflictions as well as varicose syndromes. The instant compounds retard reactions leading to edemas and swellings, including those of allergic origin.

The typical daily dosage of 10 to 300 mg results in reducing or eliminating the above afflictions, commonly within some days. A preferred dosage is 30–100 mg.

EXAMPLE 4

Preparation of pharmaceutical compositions

Composition 25 g active material according to the present invention
150 g lactose
100 g polyvinylpyrrolidone solution (5% in water)
5 g magnesium stearate
15 g sodium amylopectin glycolate The active material is carefully mixed with the lactose in a kneader, thoroughly moistened with the polyvinylpyrrolidone solution and the resultant mass is forced through a sieve with a mesh size of 1.9 mm. The resulting granules are dried and freed from coarse components by passing through a sieve with a mesh size of 1.2 mm and from fines by means of a sieve with a mesh size of 0.6 mm.

These granules can be used directly for filling hard gelatin capsules (180 mg/capsule) and administered.

Furthermore, the granules can be mixed with the magnesium stearate and the sodium amylopectin glycolate and pressed into tablets. The diameter of the tablets is 8 mm, the weight 200 mg, the hardness 2.0 kg and the content of active material per tablet is 25 mg.

The superior activity of the novel compounds is shown by comparing the inhibition of the passive cutaneous anaphylactic reaction in rats produced by injection of serum containing reaginic antibodies to egg albumin. Diethylcarbamazin, i.e., 1-diethylcarbamoyl-4-methylpiperazine was used as a comparison compound. Specifically, tests were run as follows:

Serum containing reaginic (IgE-like) antibody to egg albumin was prepared by injecting rats intramuscularly with 0.1 ml of a solution of the antigen (10 mg/ml) in saline together with 0.5 ml of Bordetella pertussis vaccine (Behring; 2 × 10$^{10}$ organisms/ml). 9–14 Days later the animals were bled from the abdominal aorta; the serum was pooled and stored at −20° C until required. The titer of the serum, i.e., the highest dilution inducing passive cutaneous anaphylaxis (PCA) in the rat following a 48-hour latent period, was between 1:8 and 1:32. For use in these experiments the serum was diluted 1:24. The reaginic nature of the antibody was demonstrated by its ability to induce PCA with a latent period in excess of 7 days and also by abolition of its PCA activity by heating it at 56° C for 1 hour.

The animals were anesthetized with 2,2-dichloro-1,1-difluoroethyl-methyl ether, sold under the trademark Penthrane, and were sensitized by injecting 0.1 ml of the antiserum into the shaved abdominal flanks. After 48 hours for reaginic PCA, the animals were given an intravenous injection of 1 ml of saline solution containing 0.5% by weight of egg albumin and 0.25% by weight of Evans Blue.

After having killed and exsanguinated the animals, the size in square millimeters and the intensity, in arbitary scores, of the resulting blue spot were determined. The product of these two parameters was used to determine the degree of the reaction and the degree of reaction with no active material was taken as the standard against which to measure % inhibition of the anaphylactic reaction.

6 Animals were used per dose level and for control.

The test material was injected intravenously immediately before the antigen, using a solution in water containing 0.5% HCl and 2% of dimethylformamide. For comparative purposes there was also tested diethylcarbamoyl-4-methylpiperazine sold under the tradename Diethylcarbamazin. The volumes of the injections were varied to give the indicated dosage of active material. The results obtained were as follows:

PCA Reaction in Rats Induced by Reaginic Antibodies (Ovalbumin 2 × cryst. and Bord. pertussis 2 × $10^{10}$) Active material applied intravenously immediately before antigen Table III

| Active Material | mg/kg | % Inhibition PCA |
|---|---|---|
| Diethylcarbamazin | 60.0 | 58 |
| Ex. 1 | 0.38 | 27 |
| Ex. 1 | 0.75 | 45 |
| Ex. 1 b | 0.38 | 32 |
| Ex. 1 e | 0.38 | 54 |
| Ex. 1 j | 0.38 | 21 |
| Ex. 1 j | 0.75 | 60 |
| Ex. 1 k | 0.38 | 21 |

The dosage schedule for blood pressure lowering is entirely dependent on the condition of the patient, his response to the treatment and whether or not he is ambulatory or hospitalized. The treatment should be begun with small doses (100 mg) and increased gradually depending upon the patient's response. The dosage can be increased at 5 to 7 day intervals until an average daily dose of 100 to 300 mg is reached. For maintenance, two to four doses a day are usually required.

In order to establish the effectiveness of the novel products of the invention as agents for reducing blood pressure, a series of tests as follows were carried out.

The following were the test methods used:

The test animals were rats into which arterial catheters had been implanted in a sterile operation via the arteria femoralis into the aorta. It was possible to measure the animals' blood pressure in the awake state directly in the blood with a transducer (Statham Transducer Type TP 23 D 6) via a carrier frequency measuring bridge. The animals were treated by administration of 10% common salt (sodium chloride) in their feed and, starting on the sixth week of their life, two injections per week of 5 mg at a time of 11-deoxycorticosteroneacetate per animal and thus developed an arterial high pressure in the median with values of 190 to 130 mm Hg. The test compounds were administered to the animals as follows: After the blood pressure control values had been determined, the animals received the test compound perorally suspended in 10 ml of 1% methyl cellulose solution in the indicated dosage and measurements were taken 4 hours after oral application of the substance.

The results are set forth in the Table below. The values set forth in the Table represent in each case the median of at least 7 individual measurements of blood pressure depression (in mm Hg) per applied substance.

Table IV

| Active Material | No. of trials | Dosage mg/kg | Maximum Blood Pressure Reduction, mm Hg |
|---|---|---|---|
| Control (none) | 8 | — | +2 ± 1 |
| α-Methyl-Dopa | 8 | 150 | −33 ± 5 |
| 1 | 8 | 25 | −76 ± 5 |
| 1a | 7 | 25 | −47 ± 7 |
| 1b | 8 | 25 | −64 ± 5 |
| 1d | 7 | 50 | −25 ± 7 |
| 1e | 7 | 25 | −60 ± 7 |
| 1g | 7 | 25 | −18 ± 4 |
| 1h | 7 | 25 | −19 ± 3 |
| 1i | 7 | 25 | −55 ± 7 |
| 1k | 8 | 25 | −49 ± 8 |
| 1m | 7 | 25 | −20 ± 6 |

Table IV-continued

| Active Material | No. of trials | Dosage mg/kg | Maximum Blood Pressure Reduction, mm Hg |
|---|---|---|---|
| 1n | 8 | 25 | −48 ± 5 |
| 1o | 8 | 25 | −67 ± 7 |
| 1p | 8 | 25 | −57 ± 8 |
| 1q | 7 | 25 | −41 ± 7 |
| 2 | 7 | 25 | −53 ± 6 |
| 2a | 7 | 25 | −35 ± 9 |
| 2b | 7 | 50 | −35 ± 11 |

The present invention also provides pharmaceutical compositions which contain at least one of the new compounds in admixture with a solid or liquid pharmaceutical diluent or carrier and, if desired, also with odoriferous, flavoring and/or coloring materials, followed by forming into, for example, tablets or dragees or, with the addition of appropriate adjuvants, suspended or dissolved in water or oil, for example olive oil.

It will be understood that the specification and examples are illustrative but not limitative of the present invention and that other embodiments within the spirit and scope of the invention will suggest themselves to those skilled in the art.

What is claimed is:

1. A 9-[3-(4-phenoxymethylpiperidino)-propyl]-adenine of the formula

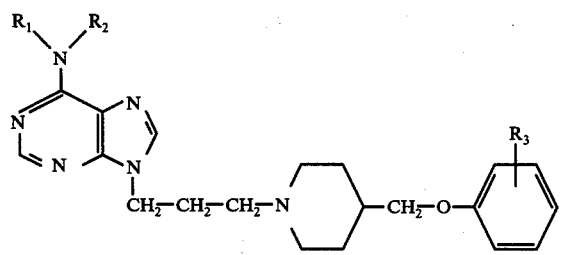

wherein $R_1$ is hydrogen or alkyl of up to 6 carbon atoms, $R_2$ is hydrogen, alkyl of up to 6 carbon atoms optionally mono-substituted by hydroxyl, or cycloalkyl of up to 6 carbon atoms, or $R_1$ and $R_2$ together with the nitrogen atom to which they are attached constitute tetramethyleneimino, pentamethyleneimino or hexamethyleneimino, and $R_3$ is hydrogen, halogen alkyl of up to 6 carbon atoms or alkoxy of up to 4 carbon atoms, in the form of the free base or a salt thereof with a pharmacologically compatible acid.

2. An adenine according to claim 1, in the form of a salt with a pharmacologically compatible acid.

3. An adenine according to claim 1, wherein such compound is 9-[3-(4-phenoxymethylpiperidino)-propyl]-adenine of the formula

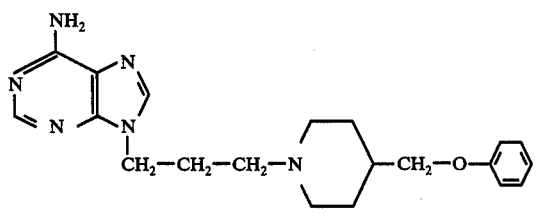

4. An adenine according to claim 1, wherein such compound is 9-{3-[4-chlorophenoxymethyl)-piperidino]-propyl}-adenine of the formula

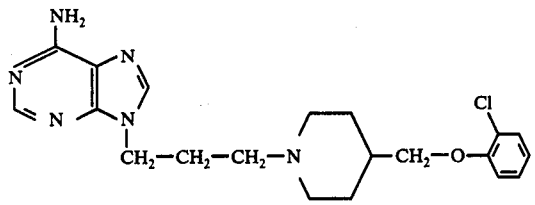

5. An adenine according to claim 1, wherein such compound is 9-{3-[4-(4-fluorophenoxymethyl)-piperidino]-propyl}-adenine of the formula

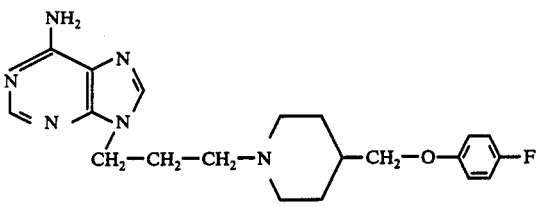

6. An adenine according to claim 1, wherein such compound is $N^6$-methyl-9-[3-(4-phenoxymethyl-piperidino)-propyl]-adenine of the formula

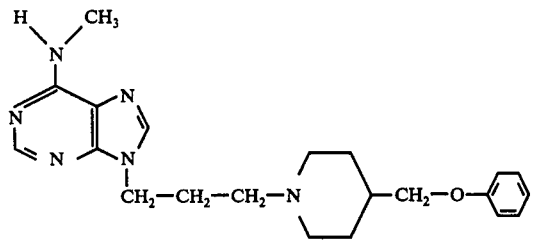

7. An adenine according to claim 1, wherein such compound is $N^6$-methyl-9-{3-[4-(4-fluorophenoxymethyl)-piperidino]-propyl}-adenine of the formula

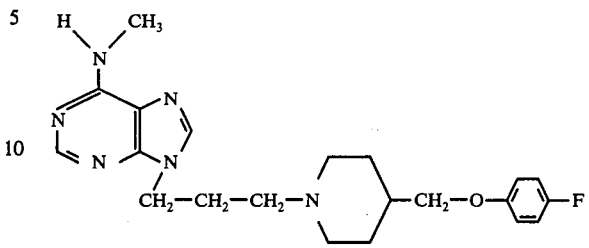

8. A composition comprising an anti-allergic, anti-inflammatory, anti-oedematous and anti-hypertensive effective amount of an adenine according to claim 1, in admixture with a pharmacologically compatible diluent.

9. A method of diminishing an allergic condition in a patient which comprises administering to such patient an anti-allergically effective amount of a compound according to claim 1.

10. The method of claim 9 wherein such compound is 9-[3-(4-phenoxymethylpiperidino)-propyl]-adenine, 9-{3-[4-(2-chlorophenoxymethyl)-piperidino]-propyl}-adenine, 9-{3-[4-(4-fluorophenoxymethyl)-piperidino]-propyl}-adenine, $N^6$-methyl-9-[3-(4-phenoxymethyl-piperidino)-propyl]-adenine or $N^6$-methyl-9-{3-[4-(4-fluorophenoxymethyl)-piperidino]-propyl}-adenine.

11. A method of diminishing an inflammatory condition in a patient which comprises administering to such patient an anti-inflammatory effective amount of a compound according to claim 1.

12. A method of diminishing an oedematous condition in a patient which comprises administering to such patient an anti-oedematally effective amount of a compound according to claim 1.

13. A method of diminishing a hypertensive condition in a patient which comprises administering to such patient an anti-hypertensive effective amount of a compound according to claim 1.

* * * * *